(12) United States Patent
Plecis

(10) Patent No.: US 8,349,159 B2
(45) Date of Patent: Jan. 8, 2013

(54) MICROFLUIDIC DEVICE FOR DETECTION OF CHARGED ANALYTES CONTAINED IN AN ELECTROLYTE AND A METHOD FOR DETECTING CHARGED ANALYTES CONTAINED IN AN ELECTROLYTE

(75) Inventor: Adrien Plecis, Bourg La Reine (FR)

(73) Assignee: Etat Francais Represente par le Delegue General pour l'Armement, Arcueil (FR)

( * ) Notice: Subject to any disclaimer, the term of this patent is extended or adjusted under 35 U.S.C. 154(b) by 512 days.

(21) Appl. No.: 12/585,767

(22) Filed: Sep. 24, 2009

(65) Prior Publication Data
US 2010/0089770 A1    Apr. 15, 2010

(30) Foreign Application Priority Data

Sep. 25, 2008    (FR) ..................... 08 05264

(51) Int. Cl.
G01N 27/447    (2006.01)
G01N 27/453    (2006.01)
(52) U.S. Cl. ........................ 204/451; 204/601
(58) Field of Classification Search .......... 204/450–455, 204/600–605
See application file for complete search history.

(56) References Cited

U.S. PATENT DOCUMENTS 5,842,787 A * 12/1998 Kopf-Sill et al. ............. 366/340
2006/0180469 A1   8/2006 Han et al.

OTHER PUBLICATIONS

Krishnamoorty et al. "Simulation and experimental characterization of electroosmotic flow in surface modified channels," Microfluid Nanofluid (2006) 2: 345-355.*
Maynes et al., "Influence of varying electroosmotic flow on the effective diffusion in electric field gradient separations," Electrophoresis 2008, 29, 549-560.*
Herr et al., "Electroosmotic Capillary Flow with Nonuniform Zeta Potential," Anal. Chem. 2000, 72, 1053-1057.*
Protoček et al., "Electroosmosis in capillary zone electrophoresis with non-uniform zeta potential," Journal of Chromatography A, 709, (1995) 51-62.*
Defintion of "intresection" downloaded on Jul. 5, 2012 from http://www.mathopenref.com/intersection.html.*
Shackman et al; Counter-flow gradient electrofocusing; Electrophoresis 2007, 28, pp. 556-571.
Kim et al; Concentration Polarization and Nonlinear Electrokinetic Flow near a Nanofluidic Channel; Physical Review Letters, PRL 99 044501 (2007) pp. 044501-1-044501-4.

(Continued)

Primary Examiner — Alex Noguerola
(74) Attorney, Agent, or Firm — Oliff & Berridge, PLC

(57) ABSTRACT

A device for selective preconcentration/detection of charged analytes contained in an electrolyte having at least two reservoirs separated by at least one rectilinear microchannel with no lengthwise axis X intersection and having at least one controllable voltage source configured to generate a potential difference between the ends of the rectilinear microchannel. The device has means for generating a controllable pressure that is associated with at least one of the reservoirs and is able to generate a pressure gradient between the two ends of the microchannel. The microchannel has, in its median part, means that are configured to generate at least one change in the surface area to volume ratio charge, the device configured to selectively concentrate the charged analytes in the median part of the microchannel upstream and/or downstream of the means configured to generate at least one change in the surface area to volume ration charge.

17 Claims, 13 Drawing Sheets

OTHER PUBLICATIONS

Datta et al; Nanofluidic channels by anodic bonding of amorphous silicon to glass to study ion-accumulation and ion-depletion effect; Talanta vol. 68 (2006) 659-665.

Van Der Wouden et al; Field-effect control of electro-osmotic flow in microfluidic networks; Colloids and Surfaces A: Physicochem. Eng. Aspects 267 (2005) 110-116.

* cited by examiner

PRECONCENTRATION ZONE FOR
OVERPRESSURE B

MICROFLUIDIC DEVICE FOR DETECTION OF CHARGED ANALYTES CONTAINED IN AN ELECTROLYTE AND A METHOD FOR DETECTING CHARGED ANALYTES CONTAINED IN AN ELECTROLYTE

BACKGROUND

The invention relates to the area of materials research or analysis using electrical means and relates in particular to a device for selective preconcentration of analytes contained in an electrolyte and also to a method for selective preconcentration of analytes contained in an electrolyte.

There are mainly two known methods for separating analytes contained in an electrolyte with the aid of microfluidic systems.

The first method is capillary electrophoresis. It is generally performed by a microfluidic network into which an electrolyte and a sample containing analytes are injected. This network may include a number of reservoirs connected to at least one long microchannel and/or to a network of microchannels having specially arranged intersections to allow a certain quantity of analytes to be injected into the center microchannel. The application of an electric field to this same channel, known as a separation channel, after the injection phase is responsible for the migration of the analytes. Under an electric field, the charged particles move in a liquid medium at a velocity defined by the field and by the mass and charge of the particles (electrophoresis). The velocity of the particles in the liquid is proportional to the electric field, the proportionality constant being called "electrophoretic mobility." At the solid/liquid interface, a double ion layer formed of a fixed ion layer (surface charge) and a mobile ion layer (diffuse layer in the liquid) forms spontaneously. Under an electric field, the ions in the mobile layer migrate, bringing about general movement of the liquid by viscosity (electro-osmosis). This movement takes place in a single block and its velocity is also proportional to the electric field. The proportionality constant between the velocity of the fluid and the electric field is called electro-osmotic mobility. The concomitant action of electrophoretic migration (velocity of ions in liquid) and the electro-osmotic liquid flow (velocity of liquid) generated by the potential difference acts on the ions contained in the fluid, ensuring that they are carried through the separation channel. The total velocity of an ion in a microchannel subjected to an electric field is hence proportional to the electric field. The proportionality constant is the total mobility of the ion which is the sum of its electrophoretic mobility (unique to each ion) and the electro-osmotic mobility (identical for all ions and dependent on the characteristics of the solid-liquid interface).

Detection of the various analytes can be carried out sequentially in time at one end of the long microchannel and gives information on the number of analytes present in the solution analyzed and their respective concentrations. This method is known for its very good resolution in separating two analytes, but has the drawback of diluting the analytes, which makes detection difficult or impossible in the case of analytes at a very low concentration.

To overcome this difficulty, a second method is known, called countercurrent gradient electrofocusing. This too employs a microfluidic network having at least two reservoirs connected to each other by channels and by at least one separation channel or chamber that concentrates the analytes in a separation channel when an appropriate pressure gradient and electric field are applied. To effect this preconcentration, there must be an electric field gradient in the central channel while the liquid flow rate is constant. Today there are several methods for creating a gradient (see Shackman and Ross, "Review Counterflow Gradient Electrofocusing," Electrophoresis 2007, 28, 556-571).

FIG. 1A shows the value of the electric field as a function of the abscissa inside a separation channel and along its lengthwise axis, and FIG. 1B shows the value of the velocity of the charged particles as a function of the abscissa inside the same separation channel and along its lengthwise axis. This velocity is the sum of their electrophoretic velocity and the velocity of the liquid. As shown in these figures, with this method the velocity of each analyte varies within the network and may become zero at one spot in the network. Thus, each analyte contained in the network migrates to the spot where its velocity is zero, at which point it is preconcentrated. Two analytes with different electrophoretic mobilities can, in theory, thus be preconcentrated in two distinct locations in the microchannel. However, this method suffers from the fact that the preconcentration zones are too wide to achieve good separation of the analytes (the preconcentration zones overlap). Moreover, the stability of the ionic gradient is often difficult to obtain (thermal or electrokinetic instabilities). Thus, this technique is used more as an overall preconcentration tool before a separation. In this case we speak of electrocapture (see Shackman et al., FIG. 5) and today no technique exists for creating an electric field gradient that is fine and stable enough to ensure appropriate separation concomitantly with preconcentration.

Also known is US Patent Application 2006/018469 by Han et al. (hereinafter Han), which describes a method combining the advantages of the two above-described methods: it has a non-selective electrocapture step followed by an electrophoretic separation step. As shown in FIG. 2, this device has two U-shaped microchannels 1, 2 at the ends of each of which is a reservoir, respectively 4, 5, 6, and 7. The respective bases 8, 9 of these two microchannels are arranged in parallel and a nanochannel 10 connects the bases of the first and second microchannels 1, 2 at their median parts 11, 12.

Platinum electrodes 13, 14, 15, 16 are disposed in each of reservoirs 4, 5, 6, and 7 and are connected to at least one voltage generator, not shown, that generates a potential difference between them. Thus, a potential difference is generated between the inlet and the outlet of the nanochannel. With such a device, displacement of the analytes is effected electrically by electrophoresis and electro-osmosis.

Embodiments also provide the use of mechanical means able to generate a pressure difference between said reservoirs 4, 5, 6, and 7, the means may, for example, be comprised of one or more micropumps and ensure movement of the solution in the device. Embodiments also provide the alternating use of electrical means for moving the solution and mechanical means for moving the solution.

The first step associated with the method described in Han consists of creating a strong non-selective preconcentration of the sample by means of a space charge region used as a barrier. When a weak electric field parallel to nanochannel 10 is generated via the first generator, applying a voltage of 1 V to reservoirs 4 and 5 and a zero voltage to reservoirs 6 and 7, no preconcentration of the compound occurs. When the electric field is increased by increasing the voltage in reservoirs 4 and 5, displacement of the ions contained in the solution occurs to a limited degree and an ion-poor zone 17 forms in microchannel 1 at right angles to nanochannel 10 in which zone there are as many negative as positive ions. When a strong electric field is applied by turning up the voltage still higher in reservoirs 4 and 5, the neutrality of the sum of the ions present in said zone 17 is no longer preserved and a space charge region is created. If the voltage in reservoir 5 is then turned down so that it is equal to half that present in reservoir 4, a secondary electric field perpendicular to nanochannel 10 is generated. Displacement of the liquid contained in said first zone 17 then occurs by electro-osmosis. The charged analytes contained in the liquid are thus transported to the space charge region, which they are unable to penetrate. Accordingly these charged analytes build up in zone 18 of the microchannel located upstream of zone 17 and before the intersection between microchannel 1 and nanochannel 10.

After this non-selective preconcentration step, Han shows that it is possible to separate the preconcentrated analytes with different electrophoretic mobilities by capillary electrophoresis.

A device according to Han has a number of drawbacks. This device does not allow selective concentration of the analytes at the intersection between the microchannel and the nanochannel (global capture) and thus requires the use of another technique and an associated device, specifically capillary electrophoresis, to separate them. This is explained by the use of a nanochannel which creates an overly strong space charge zone. Also this device is found to have secondary electro-osmosis phenomena (see Han Physical Review Letters) that disturb the space charge zone responsible for preconcentration of the species contained in the solution. These phenomena are observed in particular when the space charge zone is created. They are also caused by the non-homogeneity of the electric field due to the orthogonal connection between the microchannel and the nanochannel.

The goal of the invention is to resolve these difficulties by proposing a method and a device for implementing this method enabling the preconcentration and separation steps to be coupled through a series of selective preconcentrations of the various charged analytes contained in an electrolyte.

SUMMARY

The present application is directed to a device for selective preconcentration/detection of charged analytes contained in an electrolyte having at least two reservoirs separated by at least one microchannel with no lengthwise axis X intersection and preferably rectilinear, and having at least one controllable voltage source able to generate a potential difference between the ends of said microchannel, which device is characterized in that the device has means for generating a controllable pressure that are associated with at least one of the reservoirs and are able to generate a pressure gradient between the two ends of said microchannel and in that the latter has, in its median part, at least one first part having a constant surface area to volume ratio charge followed by a second part having means able to generate at least one change in the surface area to volume ratio charge relative to that of the first part, the device being able to selectively concentrate the charged analytes in the microchannel, upstream and/or downstream of these means.

"Surface area to volume ratio charge" is understood to mean the ratio between the average linear surface charge along the perimeter of a cross section perpendicular to the axis of this microchannel, and the area of this cross section. It is thus equal to the surface charge multiplied by the perimeter of the microchannel and divided by the cross section of the microchannel.

"Median part" is understood to mean that these means do not constitute the inlet or outlet of the microchannel.

According to one embodiment, a device according to the invention has at least one of the following additional features:

the means able to generate at least one change in the surface area to volume ratio charge along said lengthwise axis, in the shape of a step, the means able to generate at least one change in the surface area to volume ratio charge are able to generate, for a 1 mM PBS buffer electrolyte at pH 7 used as a reference electrolyte, a change in surface area to volume ratio charge that is greater than or equal to 10,000 $C/m^3$, the means that are able to generate at least one change in the surface area to volume ratio charge are able to generate it over a length, along the X axis, of less than 10 μm, the microchannel has at least one face and the means that are able to generate at least one change in the surface area to volume ratio charge are comprised either of:

at least one physical or chemical coating, only part of the face of the median part of the microchannel being covered with a coating different from that of the rest of the part (for example deposition of materials such as $Si_3N_4$, a photosensitive resin, an oxide, multilayers of charged polyelectrolytes, etc.)

a pinch in the cross section of the microchannel for only part of the median part of the microchannel, created for example by reducing its depth, whereby the smallest dimension of the microchannel must not allow formation of a charge space zone, being greater than 100 nm means able to generate a change in surface potential, for example by means of a metal-insulator-electrolyte interface able to change the effective surface charge with the aid of a radial field.

at least two microchannels disposed in parallel, each having, in its median part, means able to generate at least one change in the surface area to volume ratio charge, at least one of the ends of one of the channels being connected by a microchannel to one of the ends of the other microchannel, at least two channels have means able to generate at least one change in the surface area to volume ratio charge that differs in intensity and/or in location, an interlaced network of channels each having, between each intersection, means that are able to generate at least one change in the surface area to volume ratio charge that preferably differ in intensity and/or in location between channels, an analyte detection means that can measure their local concentration over the entire microchannel or network of microchannels over time, means for collecting and processing the data coming from said detection means, and enabling the number and concentration of the analytes contained in the electrolyte to be determined, at least one of the ends of said microchannel is connected to a mixing zone that can in particular have an internal reservoir, or a mixing coil, said mixing zone being connected to at least two reservoirs whose pressures and/or electric potentials can be controlled independently and/or containing electrolytes with different compositions.

Thus, embodiments generate ion gradients that are moderate (no charge space zone) and stable (no perturbation phenomena linked to secondary electro-osmosis) and self-generated (no need for membranes permeable to the current or temperature gradient as in field gradient electrofocusing) inside a rectilinear microchannel. To accomplish this, said microchannel thus has one or more abrupt changes in surface area to volume ratio charge within it.

An embodiment also relates to a method of selective preconcentration/detection of at least one type of analyte such as molecules, complexes of molecules or particles (artificial or biological—viruses, bacteria, spores, etc.) or cells contained in an electrolyte and implemented by a device having at least two reservoirs connected by at least said microchannel without intersection and a controllable voltage source able to generate a potential difference between the ends of said microchannel and means for generating a controllable pressure associated with at least one of the reservoirs and able to generate a pressure gradient between the two ends of said microchannel, characterized by having the following steps:

at least partly filling a first reservoir with an electrolyte containing the analytes to be selectively preconcentrated, filling at least one second reservoir disposed relative to the first reservoir on the other side of at least one rectilinear microchannel having means able to generate at least one change in the surface area to volume ratio charge, with a buffer solution that may or may not contain the investigational objects, generating a change in surface area to volume ratio charge in the median part of the microchannel with means for generating a change in surface area to volume ratio charge as well as a potential difference between the ends of said microchannel by the controllable voltage source and generating a first pressure gradient between the ends of said microchannel by the means for generating a controllable pressure, this potential difference and this pressure being able to concentrate this analyte inside said microchannel, upstream or downstream of said change in surface area to volume ratio charge, the change in volume charge being, for a 1 mM PBS buffer electrolyte at pH 7, preferably at least 10,000 C/m3.

To selectively preconcentrate two analytes with different electrophoretic velocities, one embodiment includes a method that has an additional step consisting of applying, via the controllable pressure generating means, at least one second pressure gradient able to create the preconcentration of said second analyte type in the median part of the microchannel, upstream or downstream of the means able to generate at least one change in the surface area to volume ratio charge.

DETAILED DESCRIPTION OF EMBODIMENTS

Figure 1A:
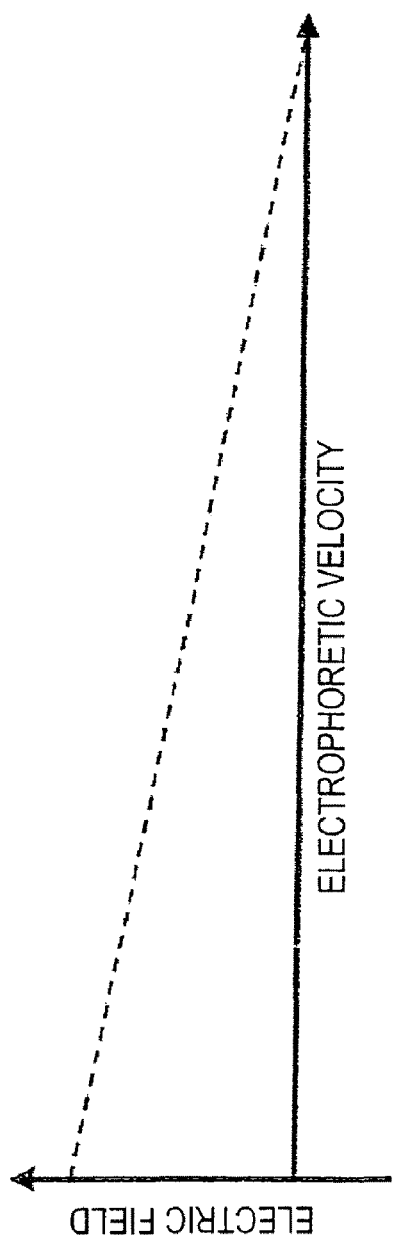
FIG. 1A shows the value of the electric field as a function of the abscissa inside a separation channel and along its lengthwise axis.
Figure 1B:
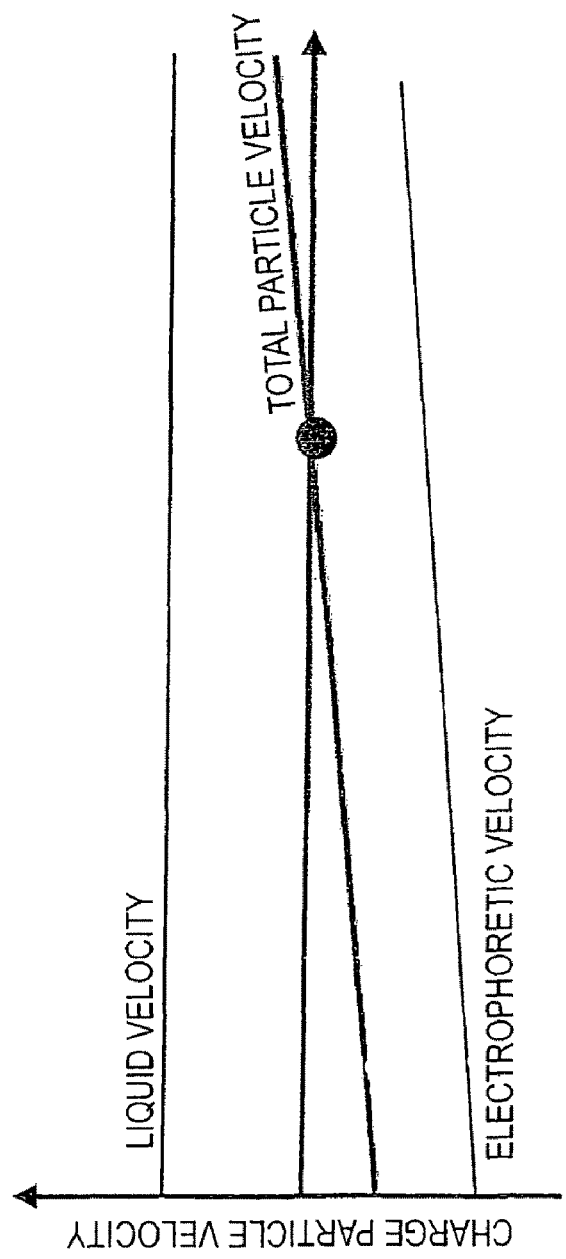
FIG. 1B shows the value of the velocity of charged particles as a function of the abscissa inside the same separation channel as in FIG. 1A, and along its lengthwise axis.
Figure 2:
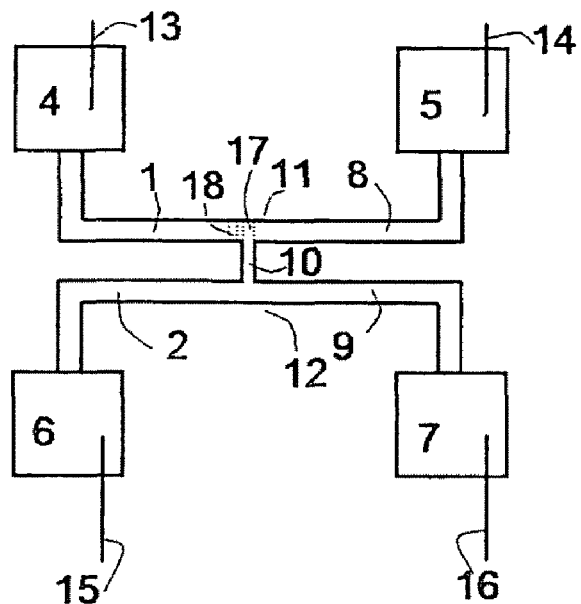
FIG. 2 shows a device with two U-shaped microchannels having a reservoir at the end of each microchannel.
Figure 3A:
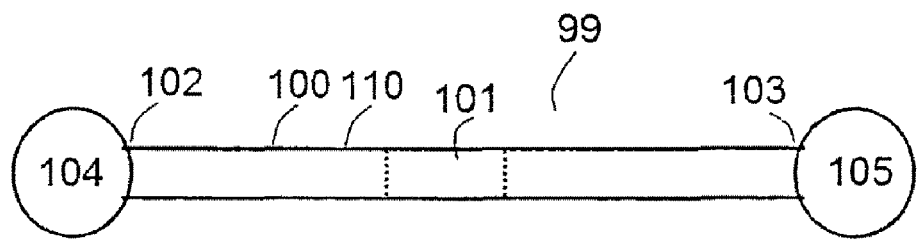
FIG. 3A shows a microfluidic network.
Figure 3B:
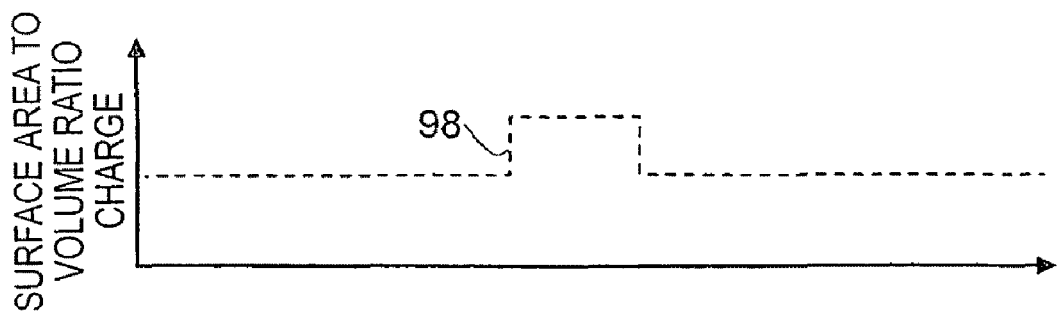
FIG. 3B shows the value of the surface area to volume ratio charge of a network in FIG. 3A.
Figure 4A:
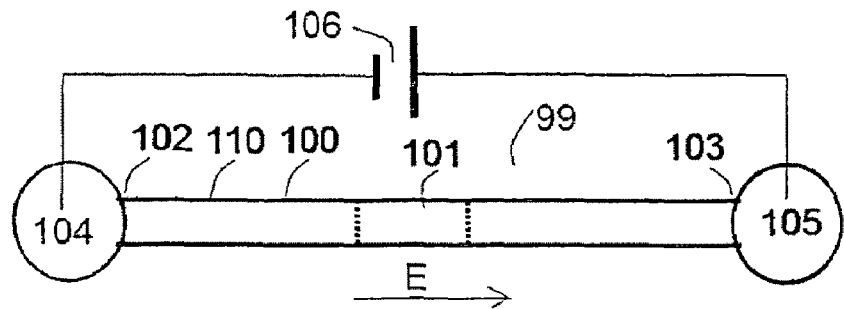
FIG. 4A shows the fluidic network of FIG. 3A to which means for generating a controllable voltage have been added.
Figure 4B:
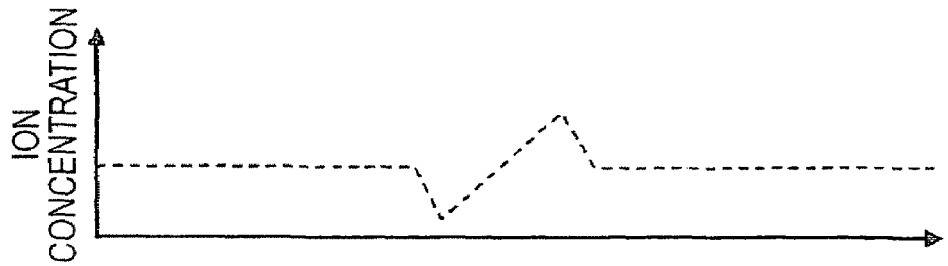
FIG. 4B shows the profile of the ion concentration of the electrolytes within the fluidic network when an electric field E is applied.
Figure 5A:
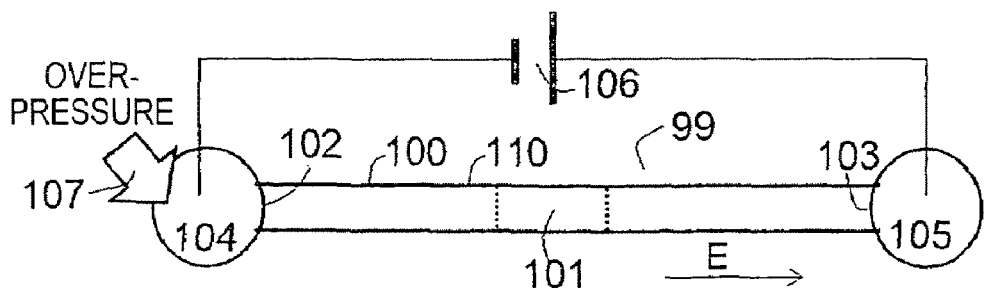
FIG. 5A shows the fluidic network of FIG. 3A to which a means for generating a pressure gradient able to generate an overpressure in the first reservoir has been added.
Figure 5B:
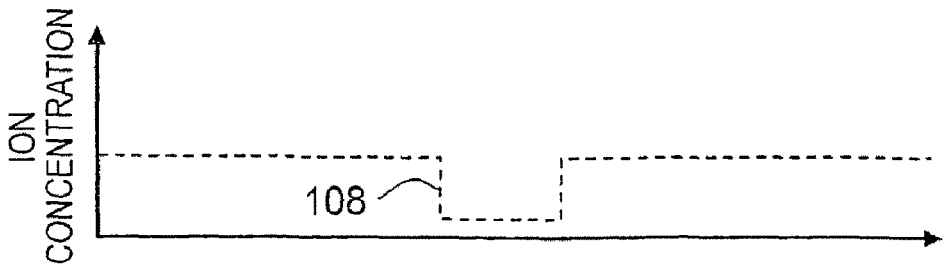
FIG. 5B shows the profile of the ion concentration of the electrolytes within the fluidic network when an electric field E and an overpressure in the first reservoir are applied.
Figure 6A:
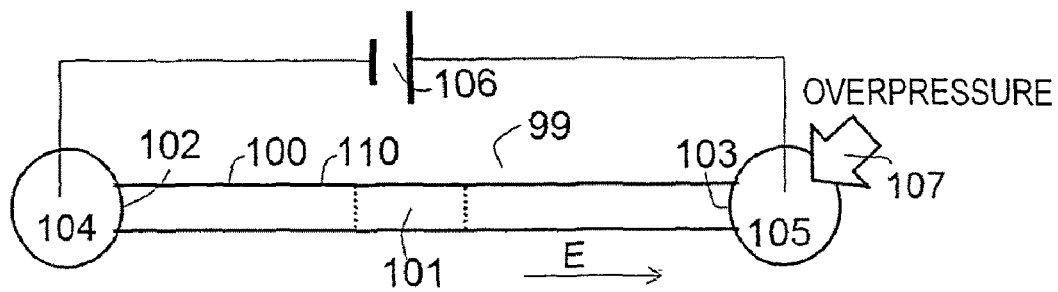
FIG. 6A shows the fluidic network of FIG. 3A where an overpressure is applied in a second reservoir located on the other side of the microchannel.
Figure 6B:
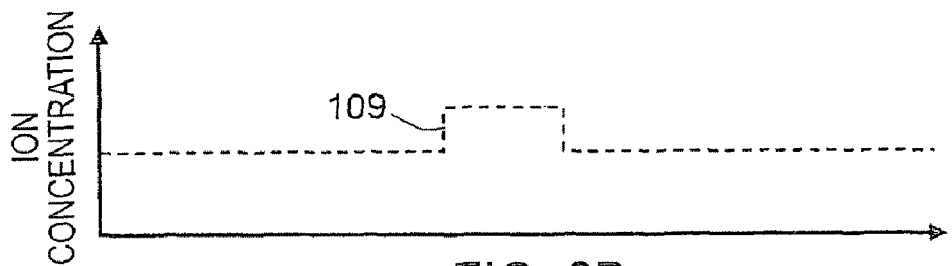
FIG. 6B shows the profile of the ion concentration of the electrolyte within the fluidic network when an electric field E and an overpressure in the second reservoir are applied.

FIG. 3A shows a microfluidic network 99 used in a device according to a first embodiment. This network 99 having a microchannel 100 that has a first part 110 having a constant surface area to volume ratio charge and ending in the median part of the microchannel and followed by means 101 able to generate a change in surface area to volume ratio charge. The ends 102, 103 of this microchannel 100 are each connected to a reservoir, 104 and 105 respectively. FIG. 3B shows the value of the surface area to volume ratio charge along such a network. The network has a first part 110 having a constant CSV. These means 101 generate a step-shaped change 98 in the surface area to volume ratio charge. When, as shown in FIG. 4A, a difference in electric potential is generated between reservoirs 104 and 105 by the means generating a controllable voltage 106, this potential difference generates an electric field directed along the lengthwise axis X of the microchannel. The abrupt change in surface area to volume ratio charge in means 101, as shown in FIG. 4B, brings about an ion concentration gradient in a part of the microchannel upstream and downstream of said means 101. If, as shown in FIGS. 5A and 6A, an electric field as well as a pressure gradient generated by means 107 and able to create a liquid flow in the microchannel is applied between the ends 102, 103 of microchannel 100, the ion concentration gradient present in surface area to volume ratio charge generation means 101 changes to assume the shape of a step either a negative step 108 as shown in FIG. 5B or a positive step 109 as shown in FIG. 6B in the overall direction of the fluid and hence on the side where an overpressure is applied. It can be seen here that a device according to the invention enables a local ion concentration gradient that is very different from the ion gradients generally obtained in electrofocusing, as shown in FIG. 1, to be generated.

The scope of this change in ion concentration depends on a number of parameters:

it increases with the degree of change in surface area to volume ratio charge, it is a decreasing function of the ion concentration of the support electrolyte, it is a decreasing function of the flow of liquid through the microchannel, it is an increasing function of the value of the electric field in the microchannel.

Figure 7A:
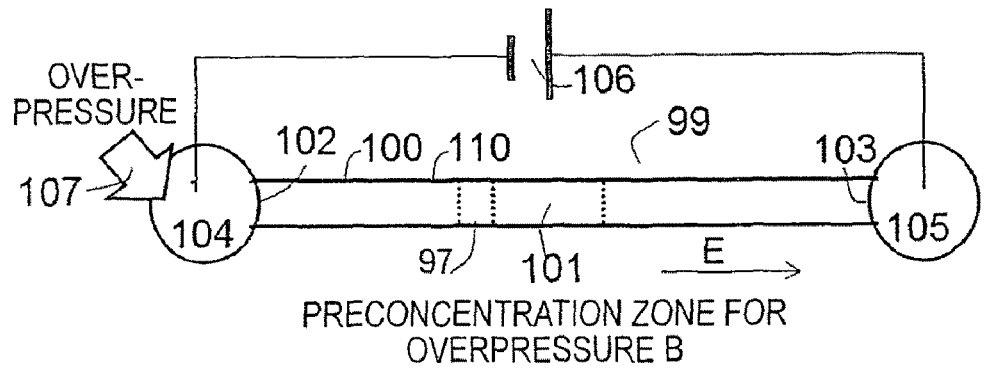
FIG. 7A shows the fluidic network of FIG. 3A where a preconcentration zone of an analyte is defined.
Figure 7B:
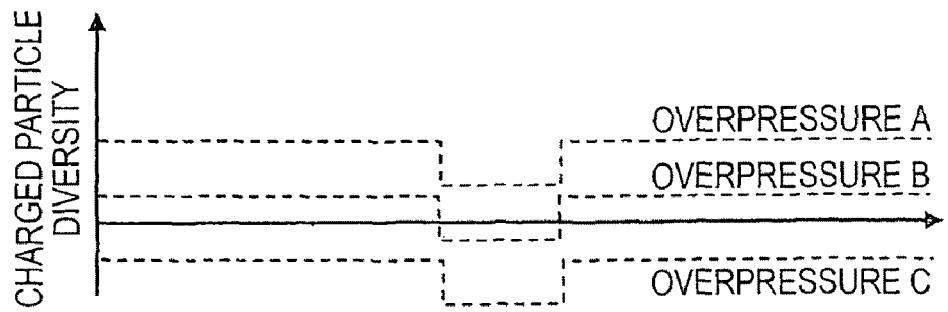
FIG. 7B shows the velocity of a charged particle with a given electrophoretic mobility for different overpressure values applied to the first reservoir.
Figure 8:
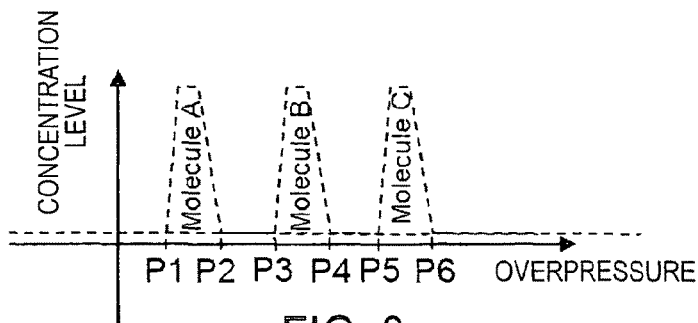
FIG. 8 shows the preconcentration levels of three analytes (having different electrophoretic velocities) as a function of the overpressure applied in said first reservoir.

This local change in ion concentration also results in a local change in the electric field. Hence, as shown in FIG. 7A which shows the microfluidic network 99 used in a device according to the first embodiment and in FIG. 7B which shows the velocity of a charged particle in microchannel 100 as a function of the overpressure value generated in reservoir 104, this velocity undergoes a local change in the means 101 that can generate a change in the surface area to volume ratio charge. It may be seen that, depending on the value of the pressure gradient applied, the liquid velocity changes, which results in translation of the velocity curve of the particle. For a certain pressure range, particularly when an overpressure is applied whose value is equal to B, the particle passes through a zero velocity zone where it is preconcentrated (zone 97 located upstream of said means 101). The main difference from customary focusing techniques is that the ion gradient, and hence the change in electric field, takes the form of a sudden step with a low height, so that preconcentration of only a very small range of electrophoretic mobility, at a very specific point, is allowed. If the overpressure is varied continuously, it is possible to sequentially preconcentrate molecules having different electrophoretic mobilities with an accuracy defined by the height of the ion barrier as shown in FIG. 8, which shows the preconcentration level in zone 97 of FIG. 7A. Thus, if the pressure gradient is made to vary continuously and increasingly in the microchannel, for example with overpressure in reservoir 104, the various analytes, in this case molecules A, B, and C, become sequentially preconcentrated in the first part of the microchannel, upstream of the means 101 for generating a change in surface area to volume ratio charge, and between a first and second overpressure P1 and P2 for molecule A, between a third overpressure P3 and a fourth overpressure P4 for molecule B, and between a fifth overpressure P5 and a sixth overpressure P6 for molecule C, with P1<P2<P3<P4<P5<P6.

Furthermore, in this geometry, the electric field always remains parallel to the microchannel axis and hence to the walls. This feature prevents formation of secondary electro-osmosis phenomena.

Figure 9A:
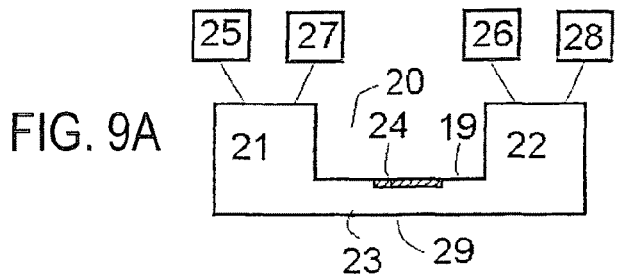
FIGS. 9A and 9B are diagrams of a device according to a second embodiment where the change in surface area to volume ratio charge is brought about with the aid of an aluminum oxide ($Al_2O_3$) layer.

FIG. 9A shows a particular arrangement of a device according to a second embodiment which is a special case of the device presented in FIG. 3A. This device 20 has a first and a second reservoir 21, 22 connected with each other by a central rectilinear microchannel 23 that is 1 cm long and has a rectangular cross section 100 μm wide and 2 μm deep. This microchannel 23, in its median part 29 and on its upper inside face 19, has an $Al_2O_3$ coating 24 that is 100 μm long.

With each of reservoirs 21, 22 is associated a controllable voltage source 25, 26, and means 27, 28 for generating a controllable pressure.

The reservoir 21 is designed to contain a specimen for analysis having molecules dispersed in an electrolyte, for example KCl. Of course, just one of the reservoirs could have a single controllable voltage source and just one controllable pressure generating means could be associated with either one of reservoirs 21, 22. The only condition is that the second reservoir be connected to the ground of said voltage source associated with the first reservoir in order to allow current to pass from the first reservoir to the second.

Figure 9B:
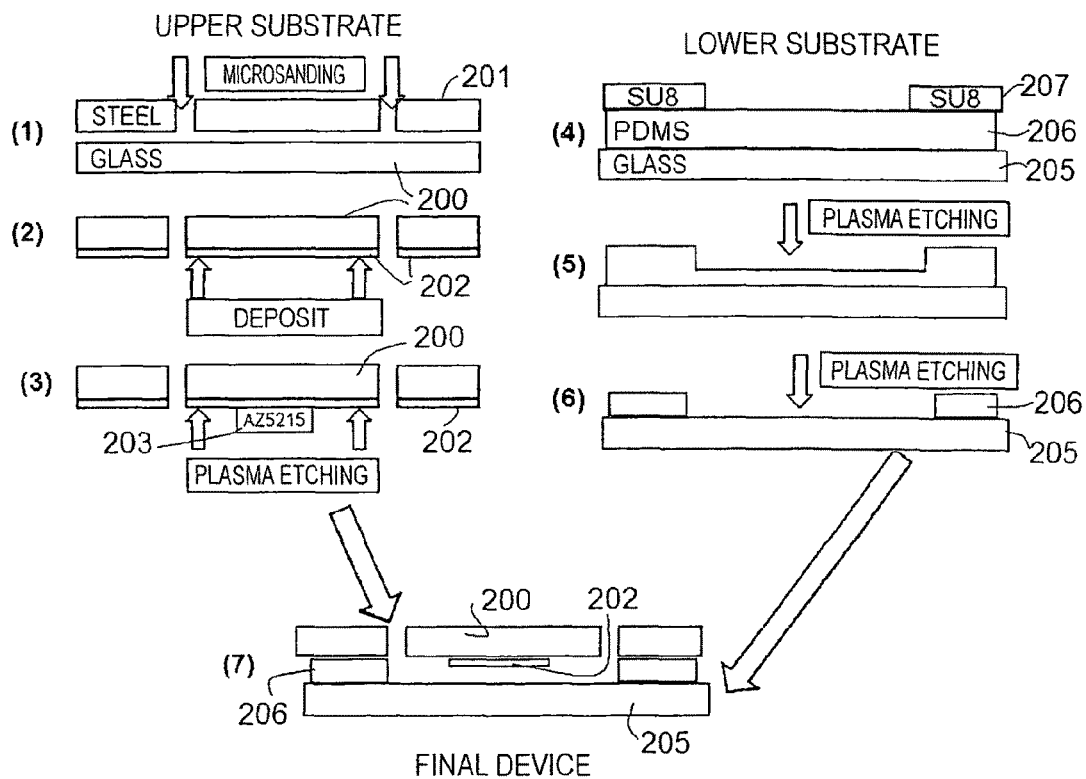

FIG. 9B shows in detail the technological steps for reduction to practice of such a device using so-called glass-PDMS-glass technology (see articles by Plecis et al. on this technology; PDMS=polydimethylsiloxane). Two D263 glass substrates, one for the lower part and the other for the upper part of the microchannel, are used. The upper substrate 200 is pierced at two points defining the ends of the microchannel by microsanding through a steel mask 201 (step 1). A thin $Al_2O_3$ layer 202, 100 nm thick, is then deposited by a deposition technique known as cathodic magnetron radiofrequency sputtering over the entire lower surface of substrate 200 (step 2). A resin mask 203 is then created by a photolithography technique using an AZ-5214 resin (Dow Corning) for example. This mask 203 is used to protect the $Al_2O_3$ layer in a plasma dry etch step that enables the $Al_2O_3$ to be removed only in the median part of the substrate 200 where the surface charge is to be varied (step 3). On the upper face of lower substrate 205 is deposited a thin layer 206 of PDMS (step 4) on which a resin layer 207 is built (for example SU-8 resin—step 5). The regions where there is no resin constitute the microchannel. A plasma etch process is then used to etch the resin and PDMS layers (step 6). The resin 207 is completely etched while a thin (2 μm) layer of PDMS 206 remains on the substrate 205, except in the region defining the microchannel. The upper and lower substrates 200, 205 are then exposed to an oxygen plasma in order to activate the surface groups of the PDMS and glass. After this activation step, the lower and upper substrates 205, 200 are aligned and brought into contact to produce a strong seal of the structure (step 7).

Figure 10A:
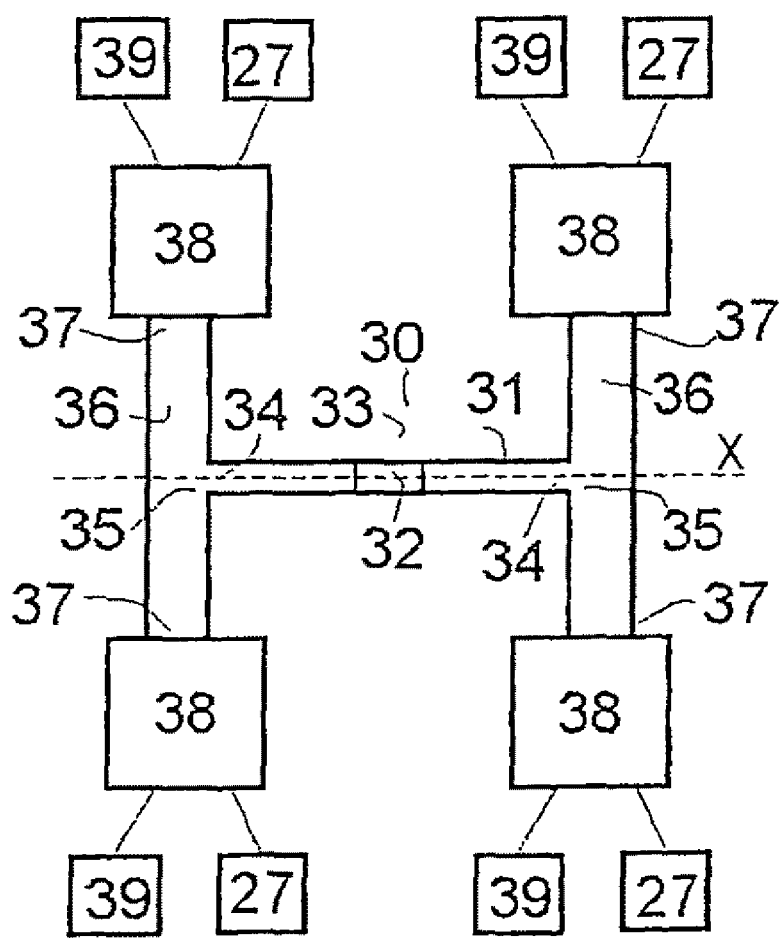
FIGS. 10A and 10B are general diagrams of a device according to a third embodiment where the change in surface area to volume ratio charge is brought about with the aid of a change in cross section.
Figure 10B:
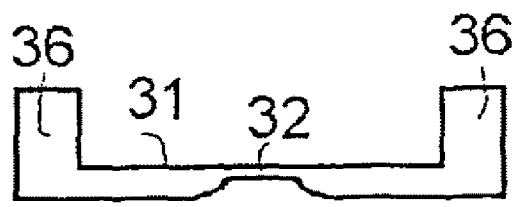

FIGS. 10A and 10B show schematically a device according to a third embodiment, FIG. 10B being a cross section through the device of FIG. 10A along the lengthwise axis (drawn as a dashed line). This device 30 has a central rectilinear microchannel 31 with an axis X and a pinch 32 in its median part 33, each of whose ends 34 is connected to the median part 35 of a mixing/injection channel 36 that has a larger cross section than microchannel 31. Each of the ends 37 of this mixing channel 36 is connected to a reservoir 38.

The microchannel 31 is 1500 µm long, 100 µm wide, and 2.5 µm deep, except at the pinch where it is only 0.5 µm deep. The length of the pinch is 50 µm.

The mixing/injection channel is 6 mm long and its cross section is 200 µm wide and 2.5 µm deep.

A controllable voltage source 39 and means 27 for generating a controllable pressure are associated with each of reservoirs 38.

An anodic bonding technique was used for reducing this device to practice. This technique is equivalent to the one described in particular by Datta et al. in his article entitled "Nanofluidic Channels by Anodic Bonding of Amorphous Silicon to Glass to Study Ion Accumulation and Ion Depletion Effect," *Talanta* 2006 68(3), pp. 659-665. It consists of etching the microfluidic sections in a Pyrex substrate using a hydrofluoric acid and HCl solution. A central microchannel 2 µm deep is thus etched into the center of the device and interrupted over a length of 100 µm. The fluid pinch is accomplished by the use of an intermediate amorphous silicon layer deposited by PECVD (plasma enhanced chemical vapor deposition) techniques. This layer is etched by SF6 plasma etching of the pre-etched microchannels, as is the region located between the two sections of the microchannel. Here it serves as a spacing layer between the upper and lower Pyrex substrate and connects the two microchannels by a fluid section whose depth is equal to that of the deposited amorphous silicon layer. For example, if the amorphous silicon layer is 0.5 µm thick it enables a central microchannel 2.5 µm deep (2µ+0.5 µm) to be created, except in a central region which is 0.5 µm deep. When the substrates are then brought into contact and heated to 400° C., and a potential (typically 600 V) is applied through the structures, permanent bonding (anodic bonding) seals the chip. The fluid access holes are made by microsanding in the upper substrate prior to the anodic bonding step.

With such a microchannel 31 and using a 1 mM PBS buffer electrolyte at pH 7, a surface charge of about 25 mC/m$^3$ is obtained. The surface area to volume ratio charge in the first part of the microchannel is equal to the surface charge multiplied by the perimeter of the channel and divided by its cross section, namely 20,500 C/m$^3$, while it is 100,500 C/m$^3$ at the pinch. The charge in surface area to volume ratio charge is hence 80,000 C/m$^3$ in this case.

Figure 11:
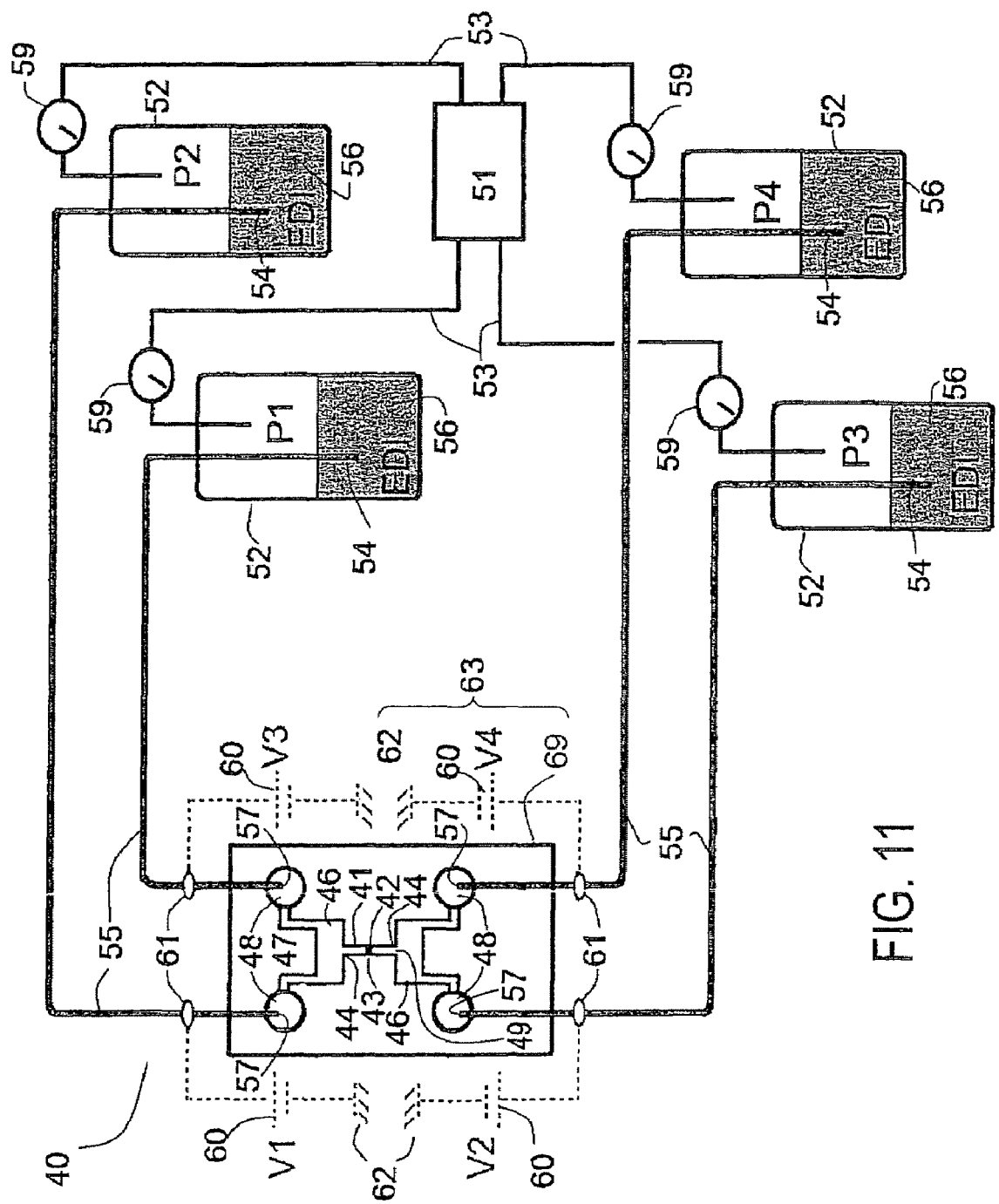
FIG. 11 is a diagram of a device according to a fourth embodiment showing in detail particularly the electrical and pressure control means external to the microfluidic chip.

FIG. 11 shows a device according to a fourth embodiment based on the same technology as described above. Only the geometry of the side channels (36 in FIG. 10A) is changed. In particular, implementation of the pressures and voltages at the various inlets is described.

This device 40 has a chip 69 that has a central rectilinear microchannel 41 having a pinch 42 in its median part 43 and each of whose ends 44 is connected to a mixing/injection channel 46 with a larger cross section than that of microchannel 41. This mixing channel 46 is U-shaped, and one of its ends 47 is connected to a reservoir 48 while the median part of its base 49 is connected to one of the ends 44 of the microchannel. A photograph of the device produced according to the method is presented in FIG. 10C.

A controllable voltage source 63 and means 50 for generating a controllable pressure are associated with each of reservoirs 48.

Each of these controllable pressure generating means 50 has a compressed air source 51 that can supply a hermetic container 52 via a supply hose 53 on which a controllable pressure gauge 59 is provided. This hermetic container 52 contains distilled water 56 and is connected by a plastic hose 55 to one of the reservoirs 48 of device 40. This plastic hose 55 has a first end 54 located at the bottom of the hermetic reservoir 52, immersed in distilled water 56, and a second end 57 immersed in the solution present in reservoir 48 of device 40. Thus, the pressure is transmitted to the reservoirs by means of water whose own pressure is regulated in independent pressure reservoirs. Each pressure reservoir is connected to a compressed air source through a programmable pressure gauge enabling the pressure to be controlled dynamically in the chamber, and hence at the inlet to the microfluidic chip comprised of the reservoirs, the mixing channels, and the rectilinear microchannel having the pinch.

The controllable voltage source has a voltage generator 60 connected on the one hand to a platinum electrode 61 disposed inside said plastic hose and on the other hand to a ground 62 common to all the voltage sources.

Several flows can be applied sequentially through this configuration:

If P1=P2>P3=P4 and V1=V2≠V3=V4, the liquid is conveyed in an equivalent quantity from reservoirs 1 and 2 to reservoirs 3 and 4. The liquid in the selective preconcentration microchannel 41 is hence a mixture of the liquids coming from reservoirs 1 and 2. If the liquids in these two reservoirs are the same, this embodiment is equivalent to that of FIG. 5A. If the liquids in reservoirs 1 and 2 are different, the liquid present in 41 will be a mixture of these two liquids, having ionic strength, pH, and analyte concentration properties that are intermediate between these two reservoirs. By modulating P1 and P2 with respect to each other (while keeping these two pressures higher than P3 and P4), it will thus be possible to modulate the composition of the liquid in the selective preconcentration microchannel 41. The potentials V1, V2, V3 and V4 can thus also be made to vary in order to modify the electro-osmotic components of the EOF flow in the side channels 46 as well as the potential distribution throughout the chip. This integration layout actually enables two "virtual reservoirs" to be created on either side of the central microchannel in the median zone of channel 46. The liquid, pressure, and electric potential composition in these "virtual reservoirs" is controlled by control parameters P1, P2, P3, P4 and V1, V2, V3, V4.

If P1=P4>P3=P2 and V1=V2=V3=V4=0, then the liquid is made to move from reservoirs 1 and 4 to replace the liquid in the side channels 46. This step can be used to change the liquid more rapidly in the chip. Likewise, the relative pressures of P1, P2, P3, and P4 can be varied at zero voltage in order to fill the chip with the electrolyte contained in one of the reservoirs. For example, if EDI is contained in reservoir 4, when P4>P1=P2=P3 is established, the device will fill with EDI (for cleaning after an analysis).

Figure 12A:
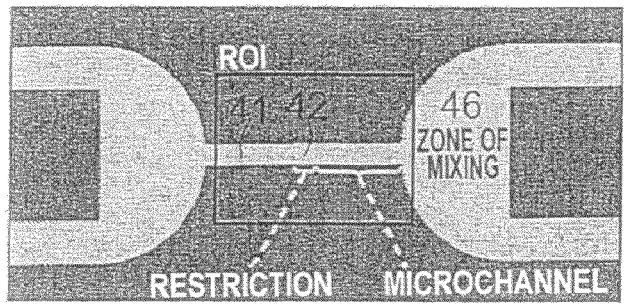
FIGS. 12A, 12B, and 12C show examples according to the FIG. 11 as well as an example of selective preconcentration monitoring by fluorescence means.
Figure 12B:
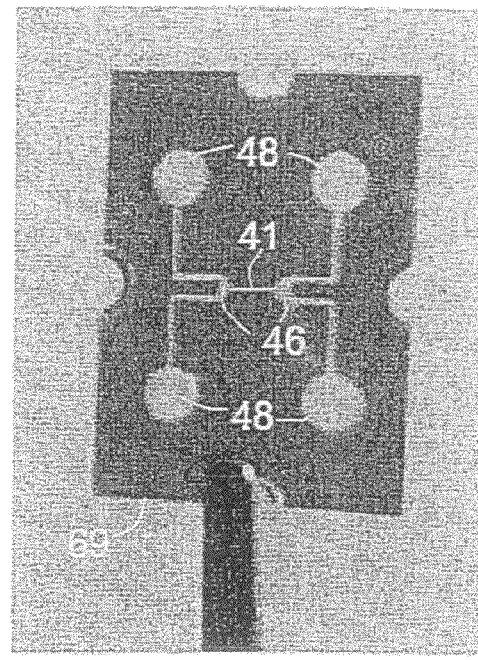
Figure 12C:
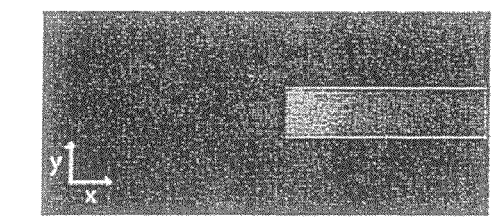
Figure 12C:
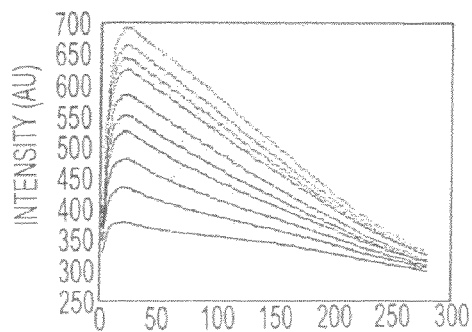

FIGS. 12A, 12B, and 12C are photographs of the embodiments associated with the diagram in FIG. 11 as well as the preconcentration curves obtained with these devices. FIG. 12A shows the central microchannel 41 with its central pinch 42 and the upstream mixing zone 46. FIG. 12B is a photograph of chip 69. FIG. 12C shows a fluorescence image of the region of interest (ROI) defined in FIG. 12A at a given instant in the selective preconcentration of a florescent probe. The curve of the intensity along the microchannel as a function of time can also be seen (the lighter curves correspond to the longer times).

Figure 13:
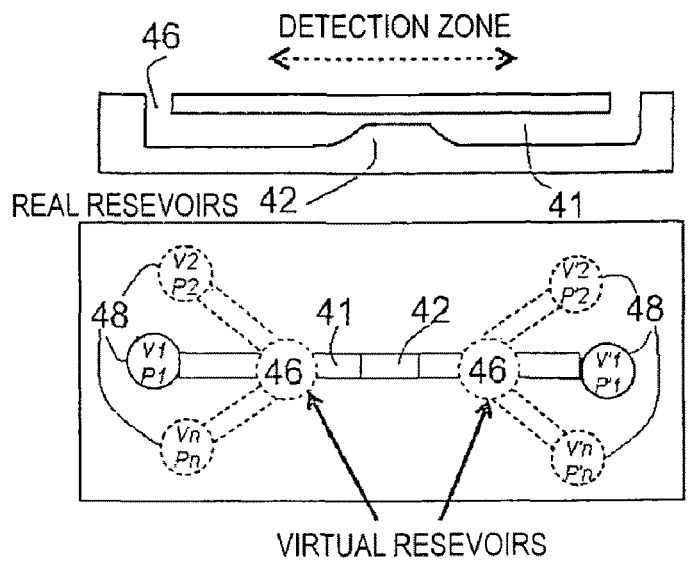
FIG. 13 is a diagram of a device according to a fifth embodiment where the choice of electric potential, pressure, and composition of the electrolyte on either side of the selective preconcentration microchannel is accomplished with the aid of so-called "virtual" or internal reservoirs connected to a certain number of external reservoirs in which the parameters referred to above are controlled individually.

As shown in FIG. 13, the mixing channels 46 can have a larger-dimension common part constituting an internal reservoir or a virtual reservoir implemented in the embodiment shown in FIG. 11, larger than microchannel 41. The composition of the electrolyte, the electric potential, and the pressure in these internal reservoirs is a function of the compositions of the electrolytes, the electric potentials, and the pressures applied in the real reservoirs, whose number may be greater than 2. Mixing means (coil or chaotic mixer) can also be added upstream of these virtual reservoirs to improve the homogeneity of the electrolyte penetrating into the microchannel where the preconcentration takes place. Also shown is the detection zone necessary for monitoring the selective preconcentration. The detection means must hence cover a detection zone corresponding to the entire microchannel where preconcentration takes place.

Figure 14:
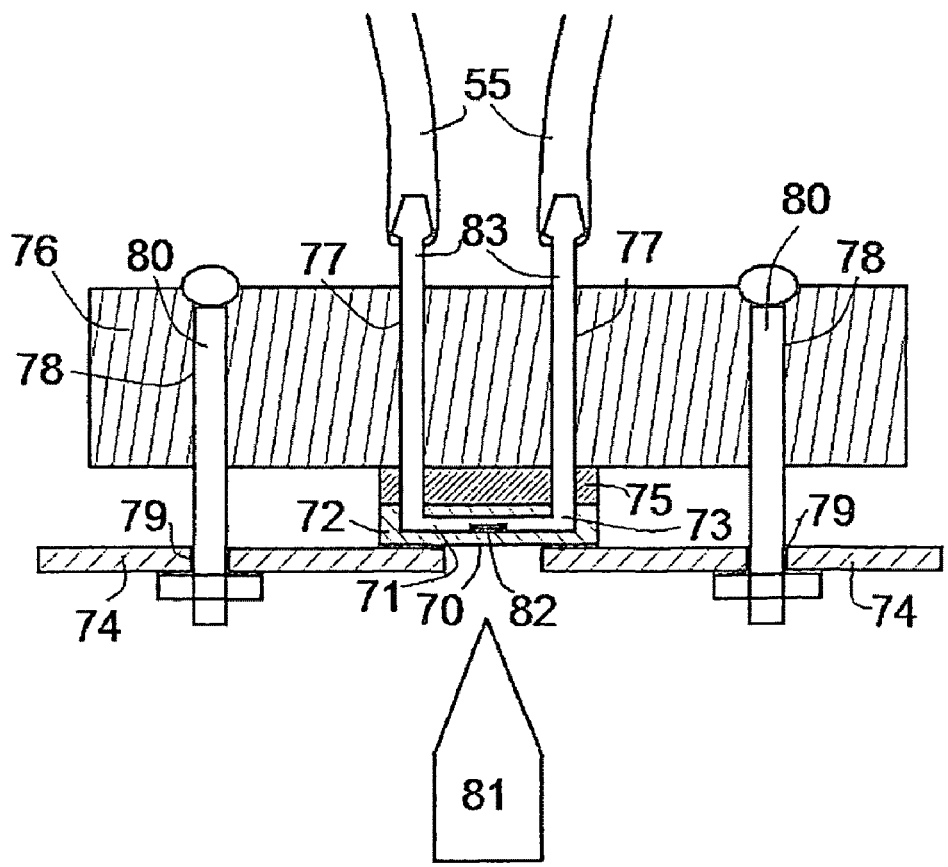
FIG. 14 is a detailed cross-sectional diagram of an embodiment of connections between a device according to a sixth embodiment and the means for generating a controllable pressure.

FIG. 14 shows, in cross section, a detailed diagram of the connections between a device according to a sixth embodiment and the means for generating a controllable pressure.

A device 70 according to this embodiment has a central rectilinear microchannel 71 embedded in a chip 72, each of whose ends is connected to a reservoir 73 ending at the upper face of the block. This block 72 is inserted between a metal plate 74 and a sealing membrane 75 having openings whose positions correspond to those of said reservoirs 73. The metal plates have the same number of bores 79 as there are coupling pin and nut assemblies 80 necessary for holding the structure. It also has a hole in its center to allow observation of the central microchannel with a microscope objective for example, 81.

A Plexiglas parallelepipedic part 76 is disposed above the sealing membrane 75. This part 76 has bores 77 that can be extensions of conduits formed by each of the reservoirs and of the opening in the membrane associated therewith. Pin and nut assemblies 80 ensure that block 72 is applied against the membrane via coaxial bores 78 and 79 created in parallelepipedic part 76 and metal plate 74, respectively. Two connecting pipes 83 integral with the Plexiglas parallelepipedic part 76 each connect one of the first bores 77 to a plastic hose 55 connected to the controllable pressure generating means.

Means 81 for detecting and determining the molecular concentration in the microchannel, upstream and downstream of the pinch 82, are associated with device 70. In this embodiment, these detection means are comprised of an epifluorescence microscope and of a CCD camera, which enable the preconcentration of the charged fluorescent molecules to be measured. In this embodiment, the liquid is injected into the bottom of the reservoirs with a syringe whose needle is inserted into bores 77.

The operation of the devices described above is as follows:

A sample of the molecules to be analyzed is mixed, if necessary, with an electrolyte solution, for example a phosphate or KCl buffer, and then placed in at least one of the reservoirs, while one or more solutions, identical or not identical to the solution to be analyzed, is placed in the other reservoir or reservoirs.

Next, a potential difference is generated, via the controllable voltage sources, between the various reservoirs. This potential difference generates an electric field parallel to the lengthwise axis X of the microchannel.

This potential difference causes displacement of the particles to be analyzed, contained in the solution inside the microfluidic network, particularly inside the rectilinear central microchannel. This displacement is a function of the electrophoretic velocity of the molecules to be analyzed and the velocity of the liquid itself. At the transition of the zone where the surface area to volume ratio charge changes, the electrophoretic velocity of the particles undergoes an abrupt change. If this change is sufficient to fully cancel out the velocity of the particle, the particle is preconcentrated. Otherwise, this particle continues on its path. In the presence of an electric field, only the electro-osmotic flow is able to displace the liquid. The liquid flowrate hence does not vary and only an electrophoretic range of molecules can be preconcentrated in this way. Hence it is essential to vary the liquid flowrate independently of the electric field.

In the context of the invention, a pressure gradient is also generated, via the controllable pressure generating means, between the various reservoirs. In this way, the liquid flowrate is modified in the preconcentration microchannel independently of the electric field, and the electrophoretic range of preconcentrated particles is modified. Application of a continuous pressure gradient that increases as a function of time thus enables the various electrically charged molecules contained in the solution that are to be analyzed to be preconcentrated sequentially.

It is thus found possible to discriminate preconcentration of the molecules present in the solution that are to be analyzed according to their electrophoretic velocity by superimposing a potential difference and causing said pressure gradient to vary. Thus, only an electrophoretic range of molecules is preconcentrated in the microfluidic part.

Selective preconcentration can take place upstream or downstream of the central pinch. It is monitored with a detection system located on the entire central microchannel in order to determine the various species present in the sample and their level. If, for example, fluorescence intensity is the detection parameter for local concentration, this intensity is measured according to a number of input variables which can be small (by causing the pressure to vary only in the reservoir where the sample to be analyzed is located) or, on the other hand, large (by causing the pressure and electric potential to vary in the various reservoirs). In the latter case, multidimensional analysis of the recorded intensity is done with more-complex digital analysis tools to determine the number of species present and their levels.

Figure 15:
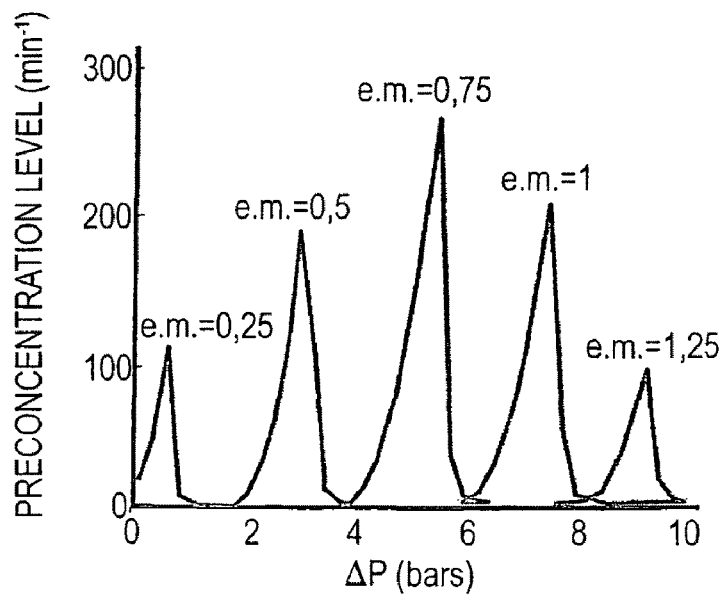
FIG. 15 shows an example of selective preconcentration as a function of the electrophoretic mobility of the molecules.

A device according to the invention allows definition of preconcentration zones in the form of bands which can be averaged in the width and depth of the central microchannel. FIG. 15 shows the preconcentration levels obtained in a device according to the embodiment illustrated by FIG. 11. In the case in point, the four reservoirs are filled with a 1 mM KCl solution containing the analytes with electrophoretic mobilities (e.m.) of 0.25, 0.5, 0.75, 1, and 1.25, respectively, times that of the fluorescent probe used for the preconcentration experiments illustrated in FIG. 12C. Here, we report the maximum preconcentration level for the entire microchannel as a function of the applied pressure gradient $\Delta P$. In these experiments, $V1=V2=0$ and $V3=V4=50V$, while $PA=P2=0$ bar and $P3=P4=\Delta P$. It can be seen that these molecules become preconcentrated for different values of $\Delta P$ which enables the preconcentration and separation steps to be coupled.

In FIG. 15, the preconcentration level is shown as a function of the pressure gradient imposed through the same central microchannel and of the KCl concentration of the electrolyte. In this case, only one analyte (e.m.=1 relative to FIG. 15) is studied. Here we can see that this molecule has a signature comprised of three preconcentration zones. By means of the embodiment illustrated in FIG. 14, which allows the ion concentration, the pH, the pressure, and the electric potential at the inlet of the preconcentration microchannel to be varied, it is possible to perform a multidimensional analysis of a sample (each molecule will have its own preconcentration signature relative to these external control parameters). Thus, it becomes possible to "extend" the preconcentration signature with the number of parameters that are varied in the inlet reservoirs of the chip.

However, it is also possible not to "extend" the signature of an analyte by multidimensional analysis, but to refine it by structuring the surface area to volume ratio charge so that it is more complex than a simple step shape.

Figure 16A:
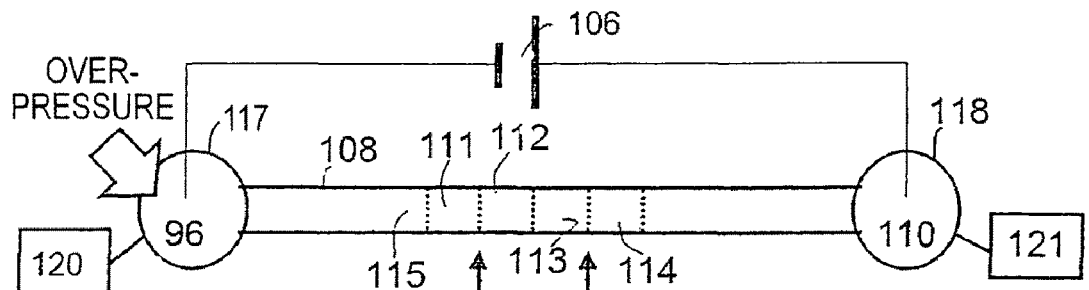
FIG. 16A shows a device according to a seventh embodiment.

FIG. 16A shows an embodiment in which one microchannel 108 is connected at each of its ends 117, 118 to a reservoir 96, and 110 respectively, and has several successive means for generating a change in surface area to volume ratio charge. Each of reservoirs 96, 110 is connected to means 120, 121 for generating a controllable pressure. In this embodiment, these means are comprised of four electrodes 111, 112, 113, and 114 located under an insulating layer (US-8 or $SiO_2$ for example). Application of a different electric potential to these electrodes enables the surface potential to be modified due to a capacitive effect (see for example the article by Van der Wouden "Field-effect control of electro-osmotic flow in microfluidic networks," *Colloids and Surfaces A: Physicochemical and Engineering Aspects*, Vol. 267, Issues 1-3, Oct. 5, 2005, pp. 110-116), hence the surface area to volume ratio charge. The chip is made with the glass-PDMS-glass technique described in FIG. 9B and a priori has dimensions similar to those in FIG. 9A. An electric potential difference is generated between the two ends 117, 118 of the microchannel via the voltage generating means 119 while an overpressure is generated in the reservoir 96 via the controllable pressure generating means 120, 121.

Figure 16B:
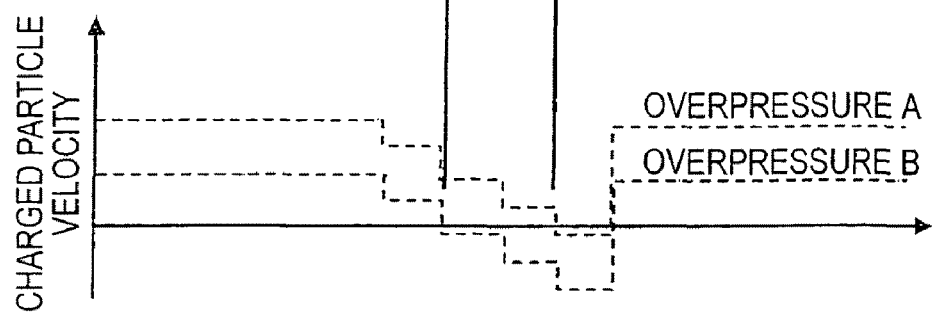
FIG. 16B shows, for two different overpressures applied to the reservoir of this device, the velocity of a charged analyte having a certain electrophoretic mobility.

FIG. 16B shows, for two different overpressures applied at the reservoir 96, the velocity of a charged analyte that has a certain electrophoretic mobility. We find that this velocity is first constant up to said upstream zone 115 then varies by leveling off with each change in surface area to volume ratio charge up to zone 116 corresponding to the fourth coating. The velocity returns to constancy downstream of these coatings and its value is equal to that of this analyte upstream of said coatings. We see that, for each of the two overpressures, the velocity of the analyte is, at a certain spot, equal to zero and that this spot varies according to the overpressure value. These spots, where the analyte velocity is equal to zero, are those where its preconcentration, and hence its separation from the other analytes, occurs. The use of a succession of surface area to volume ratio charges allows a succession of ion gradients to be created. In this case, the preconcentration zone can undergo a series of shifts when the overpressure is increased or decreased. The presence in a given microchannel of several successive means for generating a change in surface area to volume ratio charge enables the selectivity of the device to be increased.

Figure 17A:
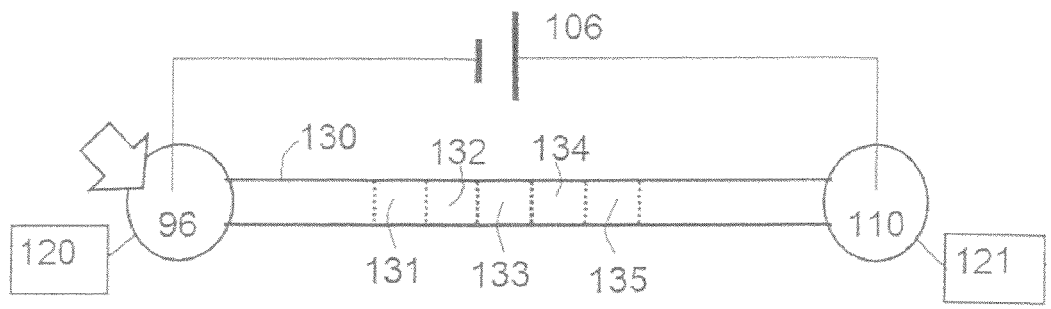
FIG. 17A shows a device according to an eighth embodiment having a microchannel that has five successive means able to generate a change in surface area to volume ratio charges.
Figure 17B:
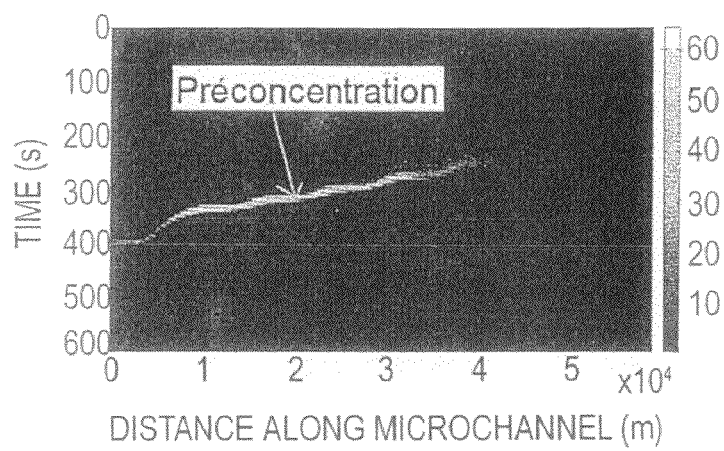
FIG. 17B shows a numerical example of preconcentration of an analyte as a function of time along this microchannel.

FIG. 17B shows digital simulation results obtained with a device having the same components as those of FIG. 6A, shown in FIG. 17A, except for a microchannel 130 that is 0.5 μm deep, has a surface charge of 0.1 $mC/m^2$, and has five successive means 131, 132, 133, 134, and 135 for generating abrupt changes in surface area to volume ratio charge producing respectively five successive surface charge zones of $-1$ $mC/m^2$, $-2$ $mC/m^2$, $-3$ $mC/m^2$, $-4$ $mC/m^2$, and $-5$ $mC/m^2$ (left to right). The total length of the microchannel is 5.4 mm and each zone is 0.2 mm long. The ion concentration (electrolyte 1:1 KCl) is 1 mM. The figure shows the concentration of a third molecule (valence=2, diffusion coefficient=$2.72^e$-10 $m^2/s$) along the microchannel as a function of time when a decreasing pressure gradient (from 1 bar to zero overpressure) is imposed in the left-hand reservoir. We see here that a preconcentration is created in the fifth zone and that the gradual decrease in pressure results in gradual displacement of this preconcentration zone over time.

Figure 18:
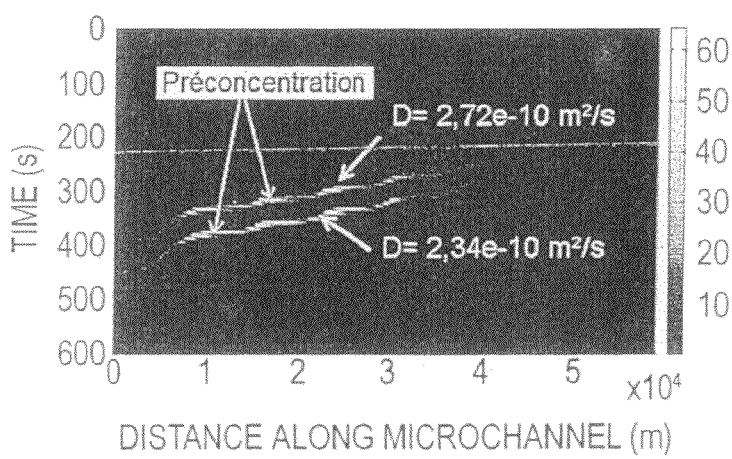
FIG. 18 shows a numerical example of preconcentration of two analytes as a function of time along the microchannel according to FIG. 17B; these analytes having similar electrophoretic velocities.
Figure 19A:
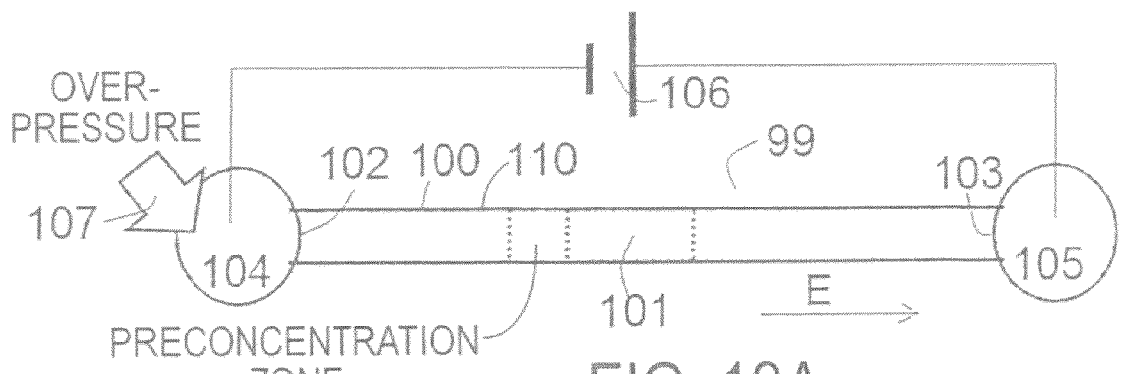
FIG. 19A shows the device of FIG. 5A.
Figure 19B:
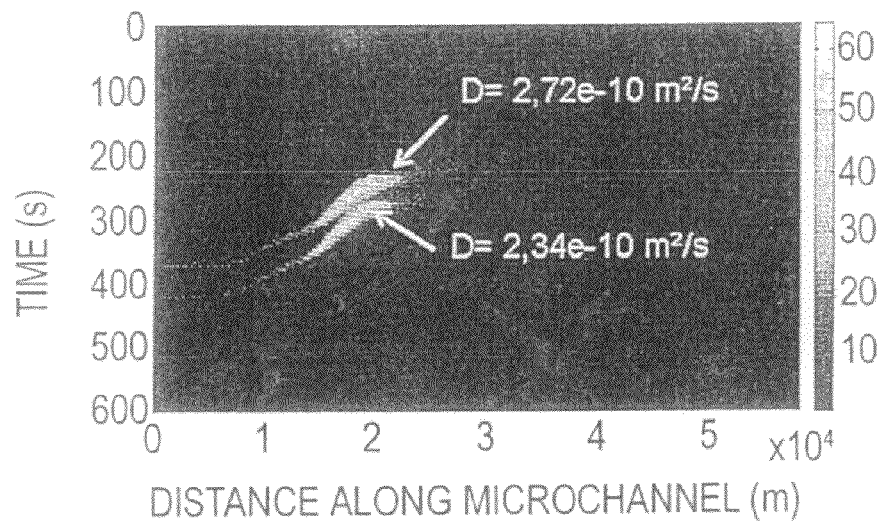
FIG. 19B shows a numerical example of preconcentration of the same two analytes as in FIG. 18B, as a function of time, along the microchannel shown in FIG. 5A.
Figure 20:
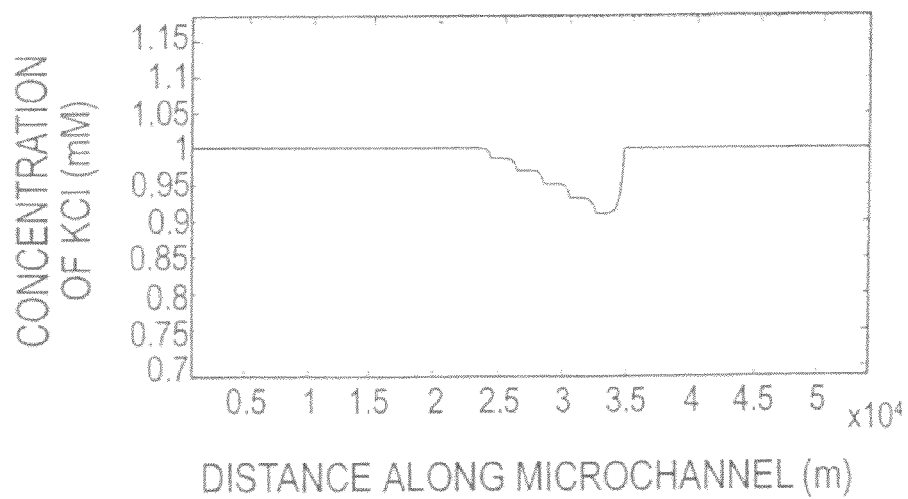
FIG. 20 shows the ion gradient obtained in the selective preconcentration experiment of FIG. 18B.

Then a second species with very similar mobility is added, we see, in FIG. 18, that temporal analysis of the local concentration enables the two molecules to be very clearly distinguished. For comparison, the same separation was carried out in the case of a single $-5$ $mC/m^2$ surface charge zone as shown in FIG. 19A. The results of this separation are presented in FIG. 19B. It is clear, by comparing FIG. 18 with FIG. 19B, that the geometry of FIG. 18 gives better discrimination between two analytes of similar mobility. FIG. 20 shows the ion gradient obtained by the selective preconcentration experiment of FIG. 18. Hence it is possible to create stable ion gradients and adapt them to the necessary resolution simply by changing the surface area to volume ratio charge along the central microchannel in successive steps.

In all cases, and for a given geometry and material of the reservoirs and the microchannel or microchannels and for given means for changing the surface area to volume ratio charge, the determination of said potential difference and of said gradient to be applied is made experimentally in advance for each analyte that could be investigated.

Figure 21:
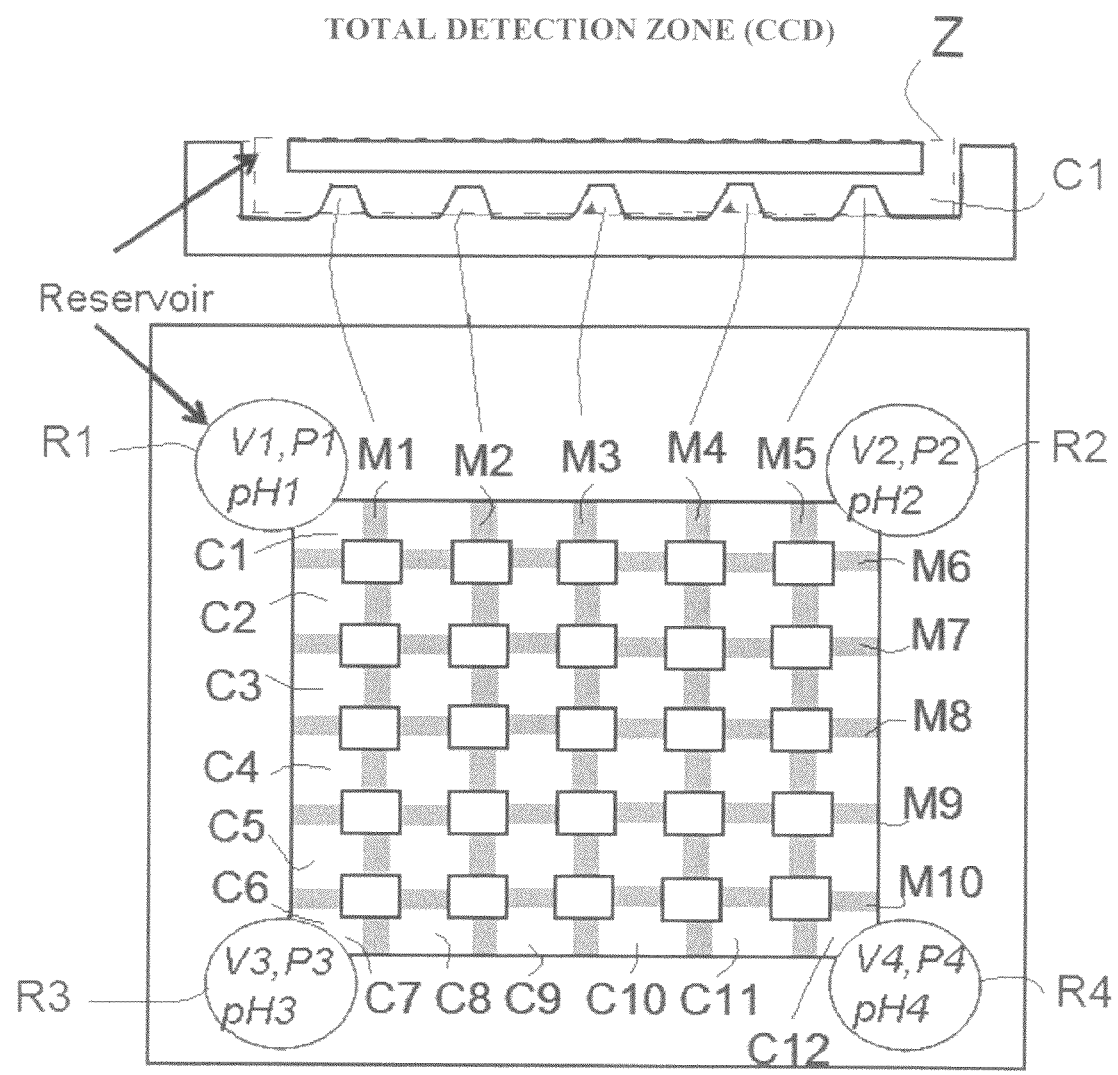
FIG. 21 shows a device according to a ninth embodiment of the invention.

Of course, numerous modifications may be made without departing from the framework of the invention. In the embodiments described above, analysis of the location and level of preconcentration is done on a chip with only one preconcentration microchannel. Of course, several preconcentration microchannels that have different variations in surface area to volume ratio charge in their median parts can be used in parallel from the same reservoirs or other reservoirs. It is also possible to envisage connecting these preconcentration microchannels to each other, thus forming a network 2D of preconcentration microchannels per surface area to volume ratio charge as shown in FIG. 21. In this embodiment, this network is comprised of six channels C1 to C6 in rows parallel to each other. Each of these channels has five means M1, M2, M3, M4, and M5 that can generate, in the microchannel, at least one change in surface area to volume ratio charge. In addition, these channels are interconnected with each other to form a second network of channels C7, C8, C9, C10, C11, C12, each of these channels being parallel with each other and in columns. Each of these channels has five means M6, M7, M8, M9, and M10 that are able to generate at least one change in surface area to volume ratio charge in the microchannel. The four ends of the channel network thus formed are each connected to a reservoir R1, R2, R3, and R4 with which controllable voltage generating means and controllable pressure generating means are associated. The zones where these microchannels meet thus constitute the same number of "virtual reservoirs" as defined in FIG. 14, in which the composition of the electrolyte, the electric potential, and the pressure depends on the composition of the electrolytes, the electric potential, and the pressure applied in each reservoir as well as the geometry of the microfluidic network. Analysis of the preconcentration intensity at each ion barrier due to the change in surface area to volume ratio charge (caused by a change in cross section and/or surface charge) allows the preconcentration signatures particular to each molecule to be observed. Finally, this figure shows in dashed lines the zone Z necessary for monitoring the selective preconcentration. The detection means must thus cover a detection zone corresponding to the entire microchannel where the preconcentration takes place.

Also, the selectivity of such an invention can be enhanced still further by superimposing, on a device according to the invention, means for generating a pH gradient through such a structure. For this purpose, one need only use support electrolytes having different pH values in the real reservoirs.

Furthermore, a method according to the invention can, for example, have a prior stage of tagging the analyte to be detected in order to facilitate its detection. For example, the addition of fluorescent antibodies to an analyte will enable the presence of antigens and the number of their variants to be determined. If there is no antigen, only the preconcentration signature of the fluorescent antibody will be found. If, on the other hand, this antibody is complexed with an analyte, its preconcentration signature will be changed and will be found in the analysis of the preconcentration figures, whether they are one-dimensional or multidimensional.

In addition, the mixing channel can also be comprised for example of a mixing coil or any other geometry that allows liquids from different reservoirs to be mingled.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A device for selective preconcentration/detection of charged analytes contained in an electrolyte comprising:
    at least two reservoirs separated by at least one rectilinear preconcentration micro channel, without intersection between two ends of the preconcentration microchannel, and with a lengthwise axis X,
    at least one controllable voltage source configured to generate a potential difference between the ends of the at least one preconcentration microchannel; and
    means for generating a controllable pressure that are associated with at least one of the reservoirs and are able to generate a pressure gradient between the two ends of the at least one preconcentration microchannel,
    wherein the at least one preconcentration microchannel has, in its median part, at least one first portion having a constant surface area to volume ratio charge followed by a second portion having means configured to generate at least one change in the surface area to volume ratio charge relative to that of the first portion.

2. The device according to claim 1, wherein the means configured to generate at least one change in the surface area to volume ratio charge is configured to generate, along said lengthwise axis X, a change in the surface charge that has a step shape.

3. The device according to claim 2, wherein the means that are configured to generate at least one change in the surface area to volume ratio charge are able to generate it over a length, along the X axis, of less than 10 µm.

4. The device according to claim 1, wherein the means configured to generate at least one change in the surface area to volume ratio charge are configured to generate, for a 1 mM PBS buffer electrolyte at pH 7, a change in surface area to volume ratio charge that is greater than or equal to 10,000 $C/m^3$.

5. The device according to claim 4, wherein the preconcentration microchannel has at least one face, and
    the means that are configured to generate at least one change in the surface area to volume ratio charge are comprised of at least one of the following elements:
    at least one coating where a part of the surface of the median part of the preconcentration microchannel is covered with a coating different from that of the rest of the median part,
    multilayers of charged polyelectrolytes,
    a substance that can be selectively deposited on only part of the surface of the median part of the preconcentration microchannel, and has a different surface charge from the rest of the median part,
    a chemical treatment applied to only part of the surface of the median part of the preconcentration microchannel and conferring thereon a different surface charge from the rest of the median part,
    a pinch in the preconcentration microchannel cross section in only one part of the median part of the preconcentration microchannel, the smallest dimension of said pinch being greater than a value of 0.1 µm,
    means configured to generate a change in surface potential in part of the surface of the median part of the preconcentration microchannel having a radial field in the median part of the preconcentration microchannel and at least one metal-insulator-electrolyte interface.

6. The device according to claim 1, wherein at least two preconcentration microchannels are disposed in parallel, and
    at least one of the ends of one of the preconcentration microchannels is connected by an additional preconcentration microchannel to one of the ends of the other preconcentration microchannel.

7. The device according to claim 6, wherein the at least two preconcentration microchannels have means configured to generate at least two changes in the surface area to volume ratio charge that differ in intensity and/or in location.

8. The device according to claim 6, further comprising an interlaced network of preconcentration microchannels each having, between each intersection, means that are configured to generate at least one change in the surface area to volume ratio charge that preferably differ in intensity and/or in location between the preconcentration microchannels.

9. The device according to claim 1, further comprising analyte detection means that can measure the analyte local concentration over the entire preconcentration microchannel or network of preconcentration microchannels over time.

10. The device according to claim 9, further comprising means for collecting and processing the data coming from said detection means, and determining the number and concentration of the analytes contained in the electrolyte within at least one of the preconcentration microchannels.

11. The device according to claim 1, wherein at least one of the ends of the at least one preconcentration microchannel is connected to a mixing zone that can have an internal reservoir, or a mixing coil, said mixing zone being connected to at least two reservoirs.

12. A method of selective preconcentration/detection of at least one type of analyte such as molecules, complexes of molecules or particles, cells, or any object with electrophoretic mobility that are contained in an electrolyte, the method implemented by a device comprising:
    at least two reservoirs connected by at least a preconcentration microchannel without intersection between two ends of the preconcentration microchannel;
    a controllable voltage source configured to generate a potential difference between the ends of the preconcentration microchannel; and
    means for generating a controllable pressure associated with at least one of the reservoirs and configured to generate a pressure gradient between the two ends of the preconcentration microchannel,
    wherein the method comprises the following steps:
    at least partly filling a first reservoir with an electrolyte containing the analytes to be selectively preconcentrated;
    filling at least one second reservoir disposed relative to the first reservoir on the other side of at least one preconcentration microchannel having means configured to generate at least one change in the surface area to volume ratio charge, with a buffer solution that may or may not contain the investigational objects;

generating a change in surface area to volume ratio charge in the median part of the preconcentration microchannel as well as a potential difference between the ends of the preconcentration microchannel by the controllable voltage source and a pressure gradient between the ends of the preconcentration microchannel by the means for generating a controllable pressure, this electrolyte distribution within the reservoirs, this change in surface area to volume ratio charge, this potential difference and this pressure gradient concentrates the analyte inside the preconcentration microchannel.

13. The method according to claim 12, wherein the method includes generation of a change in surface area to volume ratio charge of at least 10,000 C/m$^3$ within the preconcentration microchannel.

14. The method according to claim 12, wherein the selective preconcentration/detection is of at least a first and a second type of analytes,
the method comprises the following steps:
- at least partly filling a first reservoir with an electrolyte containing the analytes to be selectively preconcentrated;
- filling at least one second reservoir disposed relative to the first reservoir on the other side of a rectilinear preconcentration microchannel having means configured to generate at least one change in the surface area to volume ratio charge, with a buffer solution that may or may not contain the investigational objects;
- generating a first change in surface area to volume ratio charge in the median part of the preconcentration microchannel;
- generating a first potential difference between the ends of the preconcentration microchannel by the controllable voltage source and a first pressure gradient between the ends of the preconcentration microchannel by the means for generating a controllable pressure, this electrolyte distribution within the reservoirs, this change in surface area to volume ratio charge, this potential difference and this pressure gradient concentrates a first analyte inside the preconcentration microchannel upstream or downstream of the change in surface area to volume ratio charge; and
- filling one of the reservoirs with an electrolyte presenting a difference in composition and/or generating a second, different change in surface area to volume ratio charge in the preconcentration microchannel with the means for generating a change in surface area to volume ratio charge and/or a second, different potential difference between the ends of the preconcentration microchannel by the controllable voltage source, and/or a second, different pressure gradient between the ends of the preconcentration microchannel by the means for generating a controllable pressure, this electrolyte distribution within the reservoirs, this change in surface area to volume ratio charge, this potential difference and this pressure concentrates the second analyte inside the preconcentration microchannel, upstream or downstream of the change in surface area to volume ratio charge.

15. The method according to claim 14, including a step of changing any of the parameters between two extreme values continuously.

16. The method according to claim 15, including a step of continuous local analyte concentration measurement.

17. The method according to claim 12, additionally having the following steps:
- for each pressure gradient, measuring the local analyte concentration, and
- from the measurement of local analyte concentration, determining the number and concentration of the analytes present in the initial solution.

* * * * *